(12) United States Patent
Fripp et al.

(10) Patent No.: US 12,624,634 B2
(45) Date of Patent: May 12, 2026

(54) MONITORING WELLBORE FLUIDS USING METAL IONS FROM TRACERS

(71) Applicant: Halliburton Energy Services, Inc., Houston, TX (US)

(72) Inventors: Michael Linley Fripp, Carrollton, TX (US); Chad W. Glaesman, Singapore (SG); Stephen Michael Greci, Little Elm, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 827 days.

(21) Appl. No.: 17/357,105

(22) Filed: Jun. 24, 2021

(65) Prior Publication Data

US 2022/0412210 A1 Dec. 29, 2022

(51) Int. Cl.
| | |
|---|---|
| *E21B 47/11* | (2012.01) |
| *E21B 43/267* | (2006.01) |
| *E21B 49/08* | (2006.01) |
| *G01N 21/31* | (2006.01) |
| *G01N 33/28* | (2006.01) |

(52) U.S. Cl.
CPC ............ *E21B 47/11* (2020.05); *E21B 43/267* (2013.01); *E21B 49/086* (2013.01); *G01N 21/31* (2013.01); *G01N 33/2823* (2013.01); *G01N 33/2835* (2013.01)

(58) Field of Classification Search
CPC ...... E21B 47/11; E21B 43/267; E21B 49/086; G01N 21/31; G01N 33/2823; G01N 33/2835
See application file for complete search history.

(56) References Cited

U.S. PATENT DOCUMENTS

| | | | |
|---|---|---|---|
| 7,560,690 | B2 | 7/2009 | Stray et al. |
| 8,603,827 | B2 | 12/2013 | Zahlsen et al. |
| | | (Continued) | |

FOREIGN PATENT DOCUMENTS

| | | |
|---|---|---|
| WO | 0181914 A1 | 11/2001 |
| WO | 2004106942 A2 | 12/2004 |
| | (Continued) | |

OTHER PUBLICATIONS

Brett and Brett Electrochemistry Principles: Methods and Applications, Oxford University Press 1993, pp. 1-29 (Year: 1993).*

(Continued)

*Primary Examiner* — Maris R Kessel
*Assistant Examiner* — Valerie Simmons
(74) *Attorney, Agent, or Firm* — Kilpatrick Townsend & Stockton, LLP

(57) ABSTRACT

A wellbore tracer system can include a first tracer including a first type of metal ions, a second tracer including a second type of metal ions, and a detector positioned proximate to a surface of the wellbore. The first tracer can be positioned at a different section of the wellbore than the second tracer. The detector can analyze a sample of produced wellbore fluid to identify the section of the wellbore that is a source of the produced wellbore fluid based on determining which of the first type of metal ions or the second type of metal ions is present in the sample.

8 Claims, 5 Drawing Sheets

(56)     References Cited

U.S. PATENT DOCUMENTS

| 2003/0006036 | A1* | 1/2003 | Malone | E21B 49/08 |
| | | | | 436/27 |
| 2011/0240287 | A1 | 10/2011 | Hartshorne et al. | |
| 2011/0257887 | A1* | 10/2011 | Cooper | E21B 47/11 |
| | | | | 702/12 |
| 2015/0198038 | A1* | 7/2015 | Bartetzko | C09K 8/528 |
| | | | | 166/250.05 |
| 2015/0376997 | A1 | 12/2015 | Matherly et al. | |
| 2016/0075937 | A1* | 3/2016 | Cannan | C09K 8/80 |
| | | | | 166/250.1 |
| 2016/0272882 | A1* | 9/2016 | Stray | C09K 8/92 |
| 2017/0350225 | A1* | 12/2017 | Benoit | E21B 43/26 |
| 2018/0171782 | A1 | 6/2018 | Cox et al. | |
| 2020/0255721 | A1 | 8/2020 | Planells et al. | |

FOREIGN PATENT DOCUMENTS

| WO | WO-2016182469 | A1 * | 11/2016 | | C09K 8/80 |
| WO | 2019058098 | | 3/2019 | | |

OTHER PUBLICATIONS

PCT Application No. PCT/US2021/039493 , International Search Report and Written Opinion, Mailed on Mar. 23, 2022, 11 pages.
2S Water, AquaValid product in Oil and Gas, available at https://2swater.com/industries/oil-and-gas/ at least as early as Jan. 29, 2021, 6 pages.
DKPA202330331 , "Office Action", Sep. 12, 2024, 8 pages.
Denmark Patent Application No. PA202330331, Office Action mailed Jan. 23, 2025, 5 pages.

* cited by examiner

MONITORING WELLBORE FLUIDS USING METAL IONS FROM TRACERS

TECHNICAL FIELD

The present disclosure relates generally to wellbore operations and, more particularly (although not necessarily exclusively), to detecting dissolved metals released by tracers in wellbore fluid during wellbore operations.

BACKGROUND

In hydrocarbon exploration, a well can include a wellbore drilled through a subterranean formation for obtaining hydrocarbons, such as oil or gas, from wellbore fluid. The wellbore fluid can be produced at multiple zones in the wellbore. Chemicals may be used to determine which zone is producing oil, gas, or water. A sample of fluid with a chemical can be acquired at a wellsite and transported to a laboratory for chemical analysis, and the results can be used for determining which zone is producing oil, gas, or water. But accurately determining which zone is producing the wellbore fluid can be difficult, and real-time decisions at the wellsite cannot be made on the results since the analysis takes considerable time, including transport time. For example, high concentrations of the compounds may be necessary to be detected for accurate results. And, the process may be labor-intensive, time-consuming and may not allow for timely adjustment of production operations.

DETAILED DESCRIPTION

Figure 1:
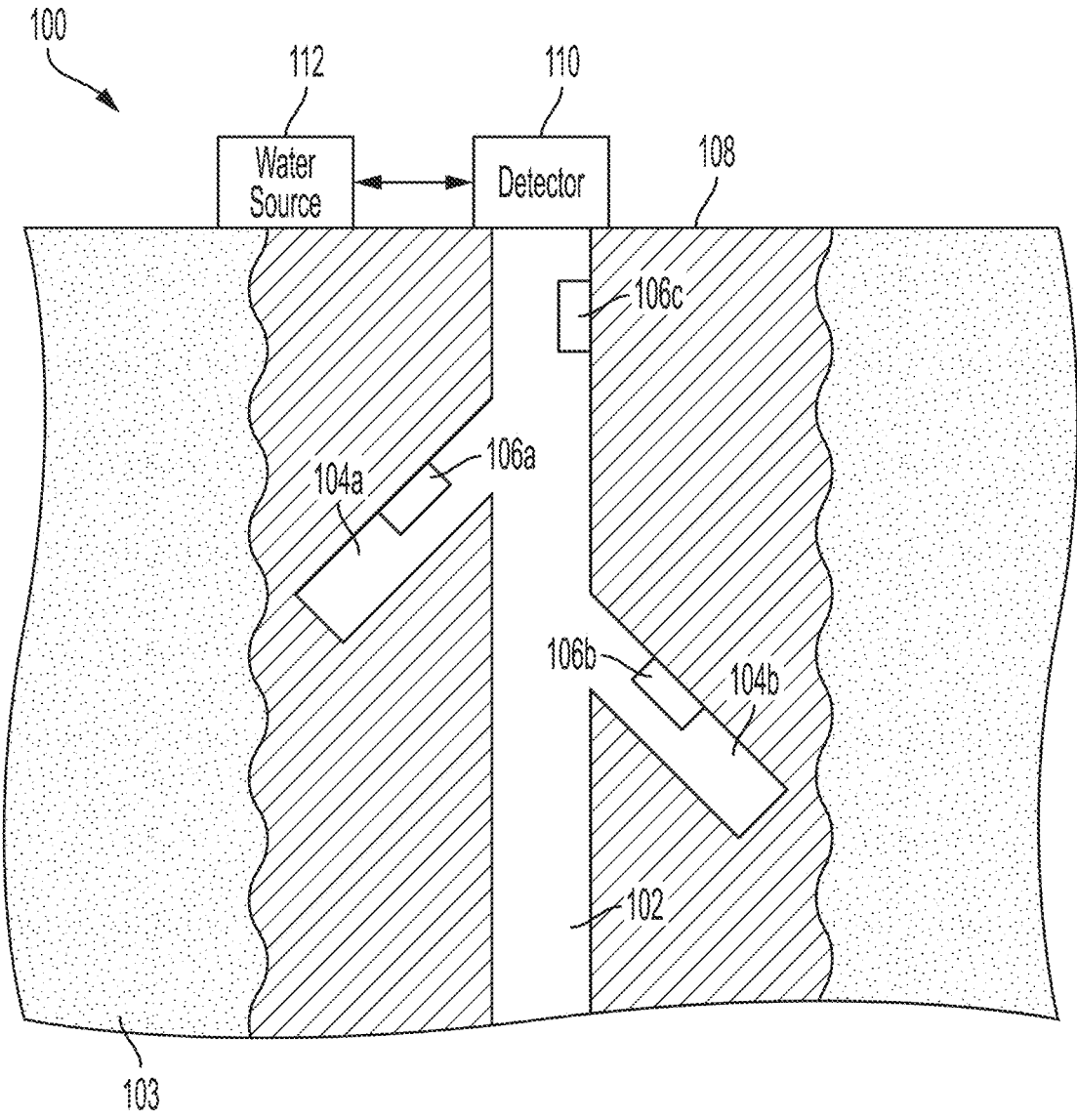
FIG. 1 is a schematic diagram of an example of a wellbore in a production environment for releasing metal ions from tracers into produced wellbore fluid according to one example of the present disclosure.

Certain examples of the present disclosure involve a real-time tracer system that can include tracers that can release dissolved metals, such as metal ions, into produced wellbore fluid that can be detected at a surface of the wellbore with a detector. As the wellbore fluid is produced to the surface, a spectrometer in the detector can analyze a sample of the wellbore fluid and detect the dissolved metals. The flow from a specific section can be determined by the detection of specific dissolved metals, or by the ratio of the detected dissolved metals. Each section of the wellbore may have a unique dissolved metal source. Alternatively, each section of the wellbore may have multiple dissolved metals and the detector may measure the combination of dissolved metals.

In some examples, metal ions released from tracers downhole can be detected at lower concentrations than the chemical compounds traditionally used. A tracer system according to some examples can operate without personnel and can provide real-time analysis of wellbore production zones without requiring samples to be sent to an off-site laboratory. The analysis can be used to make real-time changes in wellbore production, such as shutting off production from zones that are not producing oil or gas, or adjusting drawdown pressure in the wellbore.

In some examples, the tracer system can include at least two tracers that can be positioned within the wellbore. As produced wellbore fluid passes over each tracer, metal ions from the tracers can be released into the wellbore fluid. Different tracers that can release different types of metal ions can be placed within different sections of the wellbore. The tracer can include a metal ion source that can release metal ions. The metal ions can be released into the wellbore fluid as the metal ion source dissolves, degrades, or erodes. The metal ion sources can be selected to have different solubility rates. For example, metal ions with larger anionic fragments can tend to be less soluble than metal ions with smaller anionic fragments. As a result, smaller metal ions may be used for short-term measurements, while larger metal ions may be used for long-term measurements. In some examples, the metal ion source in the tracer can be bound within a binder. For example, the binder can be a dissolvable material. As the binder dissolves, the metal ions can be released into the wellbore fluid. In some examples, the detector may detect the presence of the binder in the sample of wellbore fluid.

Tracers may be positioned in various locations in the wellbore. For example, a tracer may be positioned in a wellbore including multiple production zones, with packers isolating the multiple production zones. In some examples, a tracer can be positioned on production tubing in a production zone in the wellbore, such as within a screen section. The produced wellbore fluid can flow through the screen and the tracer can release metal ions into the wellbore fluid. Some types of metal ion sources, such as metal salts, within the tracers can release metal ions as the metal ion source degrades from the wellbore fluid passing over the tracer. After the wellbore fluid flows through the screen, the wellbore fluid may flow into a tubing string in the wellbore. Alternatively, the tracer can be positioned as an insert in the tubing string, such that the tracer can release metal ions into wellbore fluid from multiple production zones that flow into the tubing string. In some examples, the tracer may include a delay barrier that can coat the metal ion source or binder to delay the point at which the tracer can begin releasing metal ions. The delay barrier may be used to allow an acidation job or to slow the release of the metal ions from the tracers during the early life of the wellbore.

The detector can include a spectrometer and an energy source. In one example, the detector can receive and filter a sample of wellbore fluid. The energy source can apply an energy, such as a high voltage, to the sample to turn the sample into a plasma. The plasma can emit radiation with light waves that are unique to different metals, and the spectrometer can detect the light waves to determine which metal ions are present in the sample of wellbore fluid. Determining which metal ions are present in the sample can indicate which zone of the wellbore produced the wellbore fluid. After determining the metal ions, the detector can eject the sample into a storage vessel or back into the wellbore. In some examples, the detector can be flushed with water to flush sample residue from the detector. The detector may be placed in a location proximate to the wellbore. For example, the detector may be positioned on the surface of the wellbore or the detector may be inserted within tubing string in the wellbore.

In another example, the tracer system may be used to analyze hydraulic fracturing fluid produced in a fracturing operation in the wellbore. Tracers may be, or included in, propping agents positioned to be released into the fracturing fluid in different fracturing zones of the wellbore. Examples of propping agents can include granular substances such as sand grains or pellets that can be carried in suspension by the fracturing fluid. Examples of pellets can include antimony or aluminum pellets. The propping agents can release different types of metal ions into the wellbore fluid as the propping agent degrades during the fracturing operation. A detector can detect the presence of the different types of metal ions to monitor the hydraulic fracturing operations. For example, detecting the presence of the different metal ions can be used to determine the source of the fracturing fluid. Alternatively, the absence of certain metal ions can indicate that there has not been enough cleanup in a certain fracturing zone of the wellbore to get the fracturing fluid out of the fracturing zone. In other examples, the tracer can be positioned within a gravel pack located in a fracturing zone in the wellbore.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a schematic diagram of an example of a wellbore system 100 in a production environment for releasing metal ions from tracers 106 into produced wellbore fluid according to one example of the present disclosure. The wellbore system 100 can include a tubing string 102 cemented into place in a subterranean formation 103. The tubing string 102 can include production zones 104a and 104b branching off of the tubing string 102. Production zone 104a can include a tracer 106a that can release a first type of metal ions into wellbore fluid produced in production zone 104a. Production zone 104b can include a tracer 106b that can release a second type of metal ions into wellbore fluid produced in production zone 104b. The wellbore fluid from production zones 104a and 104b can be produced upwards in the tubing string 102 toward a surface 108 of the wellbore system 100. A tracer 106c can be positioned in the tubing string 102 near the surface 108 of the wellbore system 100 such that the wellbore fluid produced in production zones 104a and 104b pass by the tracer 106c. The tracer 106c can release a third type of metal ions into the wellbore fluid. A detector 110 positioned proximate to the surface 108 of the wellbore system 100 and connected to the tubing string 102 can receive a sample of wellbore fluid from the produced wellbore fluid and analyze it to detect the presence of one or more types of metal ions. The detector 110 can use the presence of the one or more types of metal ions to determine which of the production zones 104 produced the sample of wellbore fluid. Water from a water source 112 can be used to flush the sample from the detector 110. Alternatively, the detector 110 can be positioned inside the tubing string 102 to receive a sample of produced wellbore fluid.

In some examples, some or all of the tracers 106 may be present in the wellbore. In some examples, tracers 106 may only be present in the production zones 104, only in the tubing string 102, only in one production zone 104, or some combination thereof. For example, a single tracer 106 may be placed between the production zones 104a and 104b. If metal ions from the tracer 106 are detected, this may indicate that the wellbore fluid is being produced in production zone 104b. Similarly, if no metal ions from the tracer 106 are detected, this may indicate that the wellbore fluid is being produced in production zone 104a.

The wellbore system 100 described herein is merely one example of a wide variety of wellbore systems in which the principles of this disclosure can be utilized. The principles of this disclosure are not limited to any of the details of the wellbore system 100, or components thereof, illustrated in the drawings or described herein. The wellbore system 100 can include other components not illustrated in this drawing.

Figure 2:
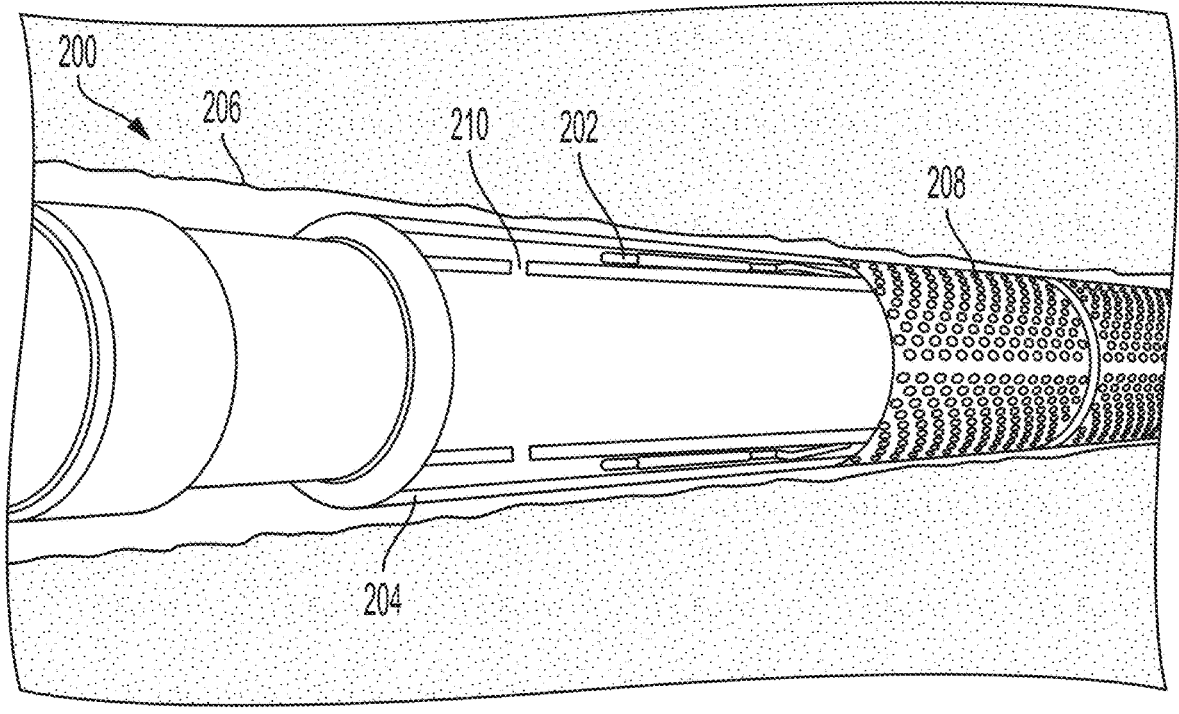
FIG. 2 is a perspective partial cutaway view of an example of a production zone in a wellbore according to one example of the present disclosure.

FIG. 2 is a perspective partial cutaway view of an example of a production zone 200 in a wellbore 206 according to one example of the present disclosure. The wellbore 206 can include production tubing 204. Tracers 202 can be mounted within a screen 208 positioned on the production tubing 204. Produced wellbore fluid can pass through the screen into the production tubing 204. As the wellbore fluid flows past the tracer 202 in the screen 208, the tracer 202 can release metal ions into the wellbore fluid through a gap 210 in the tracer 202.

Figure 3:
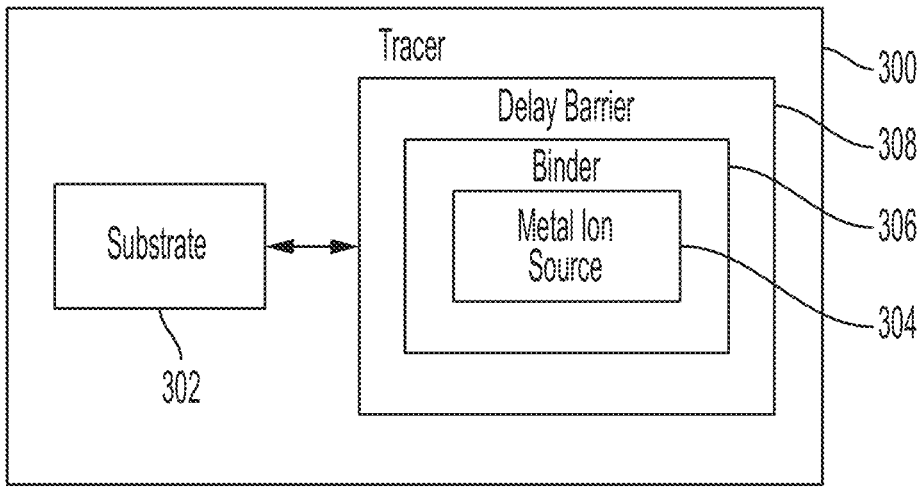
FIG. 3 is a block diagram of an example of a tracer according to one example of the present disclosure.

FIG. 3 is a block diagram of an example of a tracer 300 according to one example of the present disclosure. The tracer 300 can be positioned within a wellbore producing wellbore fluid. The tracer 300 can include a substrate 302 and a metal ion source 304. The substrate 302 can be a surface to which the metal ion source 304 is attached, such as a surface of production tubing or tubing string. Examples of metal ion sources 304 can include a metal such as magnesium or aluminum, a metal salt such as nickel chloride, a metal oxide such as zinc oxide, a metal hydroxide such as calcium hydroxide, or any other material such that there is solubility in the wellbore fluid. The metal ion source 304 can be bound within a binder 306. The metal ion source 304 can also be surrounded by a delay barrier 308 for delaying the release of metal ions into produced wellbore fluid. The metal ion source 304 may be a homogeneous metal ion source or a heterogeneous metal ion source. An example of a heterogeneous metal iron source may be a metal ion source that is layered with different metal ions. A layered heterogeneous metal ion source may result in periodic variations between different metal ion types. For example, a first metal ion source may be composed of layers of metal ions containing aluminum and layers of metal ions containing magnesium. A second metal ion source may be composed of layers of metal ions containing aluminum and layers of metal ions containing zinc. A third metal ion source may be a homogeneous metal ion source with metal ions containing aluminum. Flow past the different metal ion sources may be identified based on whether the metal ion concentration is a constant aluminum ion, is alternating between aluminum ions and magnesium ions, or whether the metal ion concentration is alternating between aluminum ions and zinc ions. As a result, more downhole locations can be uniquely identified with a smaller number of different types of metal ions.

In some examples, the binder 306 can be a polymer such as a thermoplastic, a thermoset, or an elastomer. Examples of polymers can include nylon, ethylene propylene diene monomer ("EPDM"), acrylonitrile butadiene rubber ("NBR"), hydrogenated nitrile rubber ("HNBR"), urethane, aliphatic esthers, and butyl. When bound within a polymer, the metal ion source 304 can be somewhat permeable to the wellbore fluid. For example, EPDM and butyl are permeable to oil, while many other polymers are permeable to water. The permeability can create an osmotic pressure, which can carry the metal ions out of the metal ion source 304 in the polymer and into the flow stream of the wellbore fluid.

Figure 4:
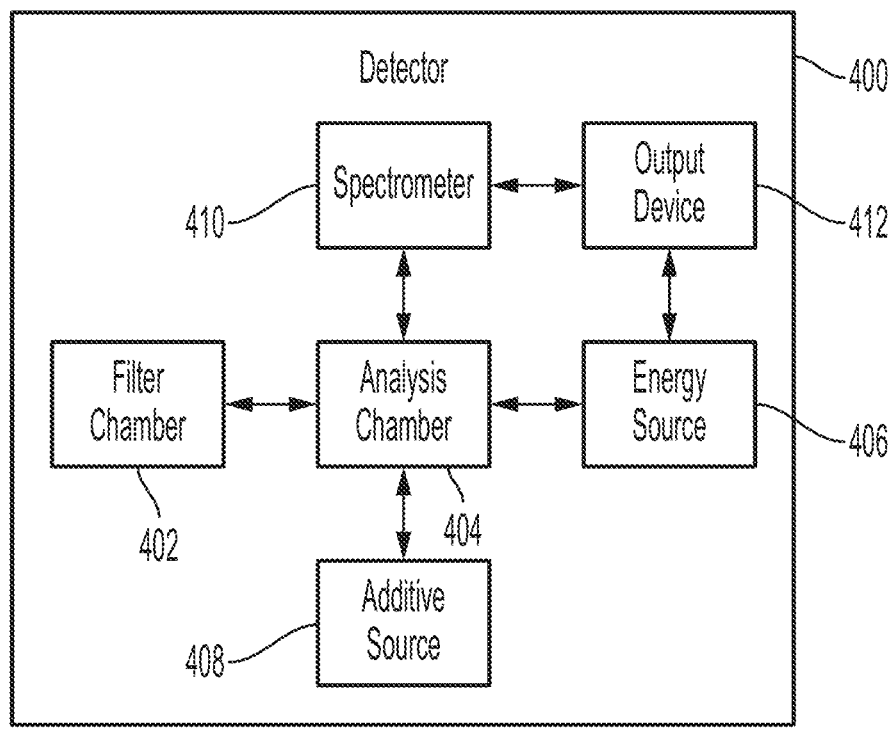
FIG. 4 is a block diagram of an example of a detector according to one example of the present disclosure.

FIG. 4 is a block diagram of an example of a detector 400 according to one example of the present disclosure. The detector 400 can include a filter chamber 402, an analysis chamber 404, an additive source 408, an energy source 406, a spectrometer 410, and an output device 412.

A sample of produced wellbore fluid from a wellbore can pass into the filter chamber 402 and the sample can be filtered to remove fine solids. The filter can also be used to select for water or oil, depending on the analysis. After filtering, the sample can move into the analysis chamber 404. The additive source 408 can add an additive, such as water, an acid, a base, a salt, or a combination thereof to the sample in the analysis chamber 404. The additive may lower the electrical resistance of the sample, which may aid in turning the sample into a plasma. The energy source 406 can apply an energy, such as a high voltage or light source, to the sample to vaporize particles within the sample into a plasma. In some examples, the voltage can be between 100 V and 10,000 V The plasma can emit radiation with wavelengths that are unique to different metals, such as metal ions released from tracers into wellbore fluid from the wellbore.

The spectrometer 410 can detect and measure the wavelengths emitted from the plasma and determine the type of metal ions present in the sample. An example of a spectrometer 410 can be an optical emission spectrometer. In one example where the detector 400 is detecting metal ions in a sample of water-based wellbore fluid, the spectrometer 410 may be able to detect metal ions present in the sample with a detection limit of 0.006 ppm for antimony, 0.1 ppm for aluminum, 0.5 ppm for zinc, and 1 ppm for copper. The detection limits may need to be higher depending on the presence of other contaminants, such as excess sodium chloride, in the sample. The detected wavelengths and type of metal ions can be output with the output device 412 to a user or computing device for determining a production zone from which the sample of produced wellbore fluid originated.

In some embodiments, the detector 400 can include a memory and a processing device that can execute one or more operations. Non-limiting examples of the processing device can include a field-programmable gate array ("FPGA"), an application-specific integrated circuit ("ASIC"), a processor, a microprocessor, etc. The processor can be communicatively coupled to the memory. The memory may include any type of memory device that retains stored information when powered off. Non-limiting examples of the memory include electrically erasable and programmable read-only memory ("EEPROM"), flash memory, or any other type of non-volatile memory. In some examples, at least some of the memory can include a non-transitory medium from which the processing device can read instructions. A computer-readable medium can include electronic, optical, magnetic, or other storage devices capable of providing the processing device with computer-readable instructions or program code. Non-limiting examples of a computer-readable medium include (but are not limited to) magnetic disk(s), memory chip(s), read-only memory ("ROM"), random-access memory ("RAM"), an ASIC, a configured processing device, optical storage, or any other medium from which a processing device can read instructions. The instructions can include processing device-specific instructions generated by a compiler or an interpreter from code written in any suitable computer-programming language, including, for example, C, C++, C#, etc.

In some examples, the operations performed by the processing device can include determining the production zone from which the sample of produced wellbore fluid originated, based on the metal ions present in the sample detected by the spectrometer 410. Alternatively, the operations can include determining the type of metal ions present in the sample based on the wavelengths detected by the spectrometer 410, as well as determining the production zone from which the sample of produced wellbore fluid originated. In some examples, the operations can include determining a flow rate of the wellbore fluid based on the amount of eroded tracer material present in the sample.

Figure 5:
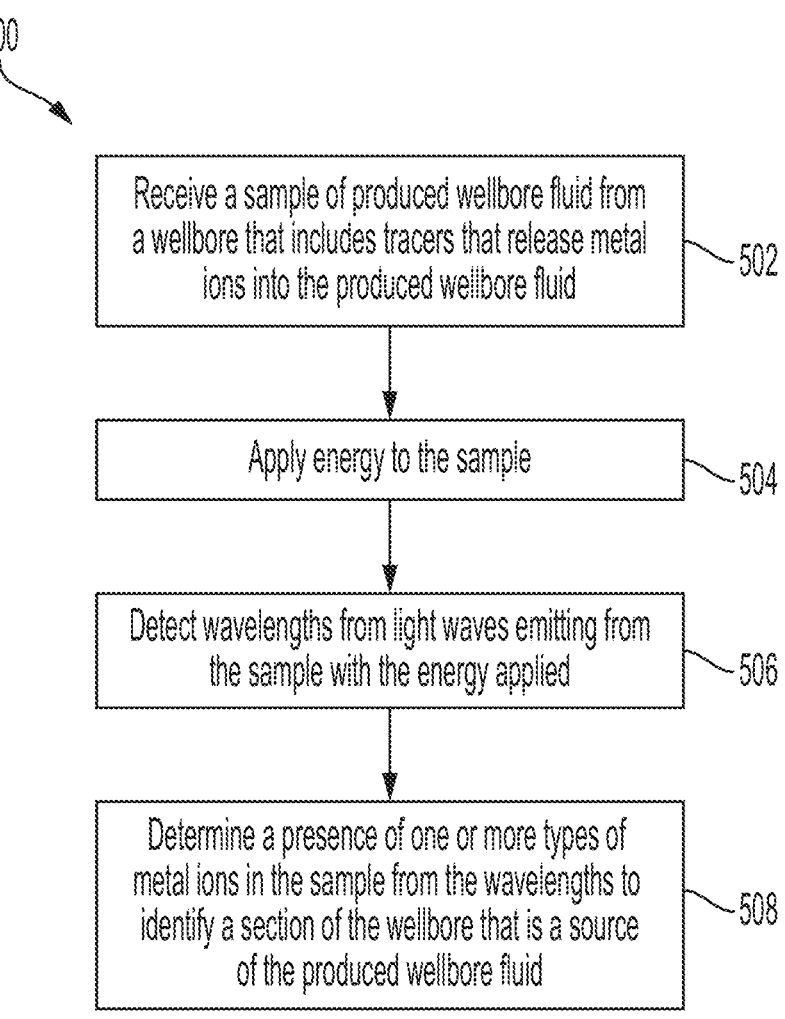
FIG. 5 is a flowchart of an example of a process for monitoring produced wellbore fluid using metal ions released from tracers into the wellbore fluid according to some aspects of the present disclosure.

FIG. 5 is a flowchart of an example of a process 500 for monitoring produced wellbore fluid using metal ions released from tracers into the wellbore fluid according to some aspects of the present disclosure. In block 502, a detector positioned proximate to the surface of a wellbore can receive a sample of produced wellbore fluid from the wellbore that includes tracers that release metal ions into the produced wellbore fluid. The tracers can be positioned at different sections of the wellbore and each release a different type of metal ion. The detector can be positioned on the surface and attached to the wellbore. Alternatively, the detector can be positioned within a tubing string of the wellbore.

In block 504, the detector can apply an energy to the sample. For example, a high-energy voltage applied to the plasma can vaporize particles within the sample to generate a plasma. The high-energy voltage can be supplied by a direct current. Alternatively, the energy can be supplied by a radio frequency power amplifier that can convert a low-power radio-frequency signal to a higher power signal that can vaporize particles within the sample to generate a plasma. The plasma can emit light waves.

In block 506, the detector can detect the wavelengths of the light waves emitting from the sample using a spectrometer. The detector can include a spectrometer for detecting and measuring the wavelengths. Patterns of wavelengths of emitted light waves can correspond to unique metals, such as the metals released by the tracers in the wellbore.

In block 508, the detector can determine a presence of one or more types of metal ions in the sample from the wavelengths to identify a section of the wellbore that is a source of the produced wellbore fluid. In some examples, the spectrometer can identify metal ions in the samples using the detected patterns of wavelengths in the emitted light, and use the identified metal ions to identify a section of the wellbore including a corresponding metal ion source. Alternatively, the detector can contain a computing device that can identify the metal ions using the patterns of wavelengths detected by the spectrometer, and use the identified metal ions to identify a section of the wellbore including a corresponding metal ion source.

In some aspects, a wellbore tracer system, a method, and a tracer for monitoring wellbore fluids are provided according to one or more of the following examples:

Example #1: A wellbore tracer system can include a first tracer, a second tracer, and a detector. The first tracer can include a first type of metal ions. The second tracer can include a second type of metal ions and be positionable at a different section of a wellbore than the second tracer. The detector may be positionable proximate to a surface of the wellbore. The detector may analyze a sample of produced wellbore fluid to identify the section of the wellbore that is a source of the produced wellbore fluid based on determining which of the first type of metal ions or the second type of metal ions is present in the sample.

Example #2: The system of Example #1 may feature the detector being positionable proximate to the surface of the wellbore to analyze the sample substantially contemporaneously to acquiring the sample from the produced wellbore fluid.

Example #3: The system of any of Examples #1-2 may feature the detector including an analysis chamber, an energy source, a spectrometer, and an output device. The analysis chamber may receive the sample from the wellbore. The energy source may apply energy to the sample. The spectrometer may detect a plurality of wavelengths from light waves emitting from the sample. The output device may output the plurality of wavelengths detected by the spectrometer.

Example #4: The system of any of Examples #1-3 may feature the detector including additives usable to lower an electrical resistance of the sample. The system may feature the energy source being a voltage or a light source.

Example #5: The system of any of Examples #1-4 may feature the plurality of wavelengths output by the detector being usable to determine a flow rate of the produced wellbore fluid.

Example #6: The system of any of Examples #1-5 may feature at least one of the first tracer or the second tracer being positionable inside and at different sections of a tubing string in the wellbore.

Example #7: The system of any of Examples #1-6 may feature the first tracer and the second tracer being positionable and on a production tubular and at different production zones in the wellbore for releasing the first type of metal ions and the second type of metal ions, respectively, into the produced wellbore fluid in respective production zones.

Example #8: The system of any of Examples #1-7 may feature at least one of the first tracer or the second tracer being in a propping agent positionable in a hydraulic fracturing fluid usable in a hydraulic fracturing process in the wellbore. The system may feature the detector being positionable proximate to the surface of the wellbore to analyze a sample of the hydraulic fracturing fluid.

Example #9: A method can include receiving, from a wellbore that includes at least two tracers that each release a type of metal ions into a produced wellbore fluid, a sample of produced wellbore fluid. The method can include applying, using a detector, energy to a sample. The method can include detecting, using the detector, a plurality of wavelengths from light waves emitting from the sample with the energy applied. The method can include determining, using the detector, a presence of one or more types of metal ions in the sample from the plurality of wavelengths to identify a section of the wellbore that is a source of the produced wellbore fluid.

Example #10: The method of Example #9 may feature the detector being positioned proximate to a surface of the wellbore to analyze the sample substantially contemporaneously to acquiring the sample from the produced wellbore fluid.

Example #11: The method of any of Examples #8-9 may feature the detector comprising an analysis chamber, an energy source, a spectrometer, and an output device. The analysis chamber may be positioned to receive the sample from the wellbore. The energy source may be usable to apply energy to the sample. The spectrometer may be usable to detect the plurality of wavelengths from light waves emitting from the sample. The output device may output the plurality of wavelengths detected by the spectrometer.

Example #12: The method of any of Examples #9-11 may feature the detector further including additives usable to lower an electrical resistance of the sample. The method may feature the energy source being a voltage or light source.

Example #13: The method of any of Examples #9-12 may feature the plurality of wavelengths output by the detector being usable to determine a flow rate of the produced wellbore fluid.

Example #14: The method of any of Examples #9-13 may feature at least one of the at least two tracers being positioned inside and at different sections of a tubing string in the wellbore.

Example #15: The method of any of Examples #9-14 may feature the at least two tracers being positioned and on a production tubular and at different production zones in the wellbore for each releasing a type of metal ions into the produced wellbore fluid in respective production zones.

Example #16: The method of any of Examples #9-15 may feature at least one of the at least two tracers being in a propping agent positioned in a hydraulic fracturing fluid usable in a hydraulic fracturing process in the wellbore. The method may feature the detector being positioned proximate to the surface of the wellbore to analyze a sample of the hydraulic fracturing fluid.

Example #17: A tracer can include a substrate positionable in a section of a wellbore and a metal ion source coupled to the substrate. The metal ion source may be positionable with the substrate in the wellbore to release, as a produced wellbore fluid in the wellbore passes by the substrate, a plurality of metal ions from the metal ion source into the produced wellbore fluid. The plurality of metal ions may be detectable by a detector positionable proximate to a surface of the wellbore.

Example #18: The tracer of Example #17 may feature the metal ion source being positionable within a binder. The binder may be a dissolvable material positionable to dissolve into the produced wellbore fluid. The metal ion source may be positionable to release the plurality of metal ions into produced wellbore fluid as the binder dissolves.

Example #19: The tracer of any of Examples #17-18 may feature the binder being a degradable material positionable to be degraded by the produced wellbore fluid. The tracer can include the metal ion source being positionable to release the plurality of metal ions into the produced wellbore fluid as the binder degrades.

Example #20: The tracer of any of Examples #17-19 may feature a delay barrier positionable to coat the metal ion source to delay the release of the plurality of metal ions.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A wellbore tracer system comprising:
   a first tracer comprising a first layer of a first type of metal ions and a second layer of a second type of metal ions, wherein the first tracer is positionable at a first production zone of a wellbore and is configured to release at least one of the first type of metal ions from the first layer or the second type of metal ions from the second layer into produced wellbore fluid in the wellbore, wherein the first layer is positioned atop the second layer within the first tracer;

a second tracer comprising the first type of metal ions, the second type of metal ions, or a third type of metal ions, wherein the second tracer is positionable at a second production zone of the wellbore that is different from the first production zone, wherein the second tracer is configured to release at least one of the first type of metal ions, the second type of metal ions, or the third type of metal ions into the produced wellbore fluid; and a detector positionable proximate to a surface of the wellbore and configured to analyze a sample of the produced wellbore fluid to identify the first production zone or the second production zone of the wellbore that is a source of the produced wellbore fluid based on determining which of the first type of metal ions, the second type of metal ions, or the third type of metal ions is present in the sample.

2. The system of claim 1, wherein the detector is positionable proximate to the surface of the wellbore to analyze the sample contemporaneously to acquiring the sample from the produced wellbore fluid.

3. The system of claim 1, wherein the detector comprises:

an analysis chamber positionable to receive the sample from the wellbore;

an energy source usable to apply energy to the sample;

a spectrometer usable to detect a plurality of wavelengths from light waves emitting from the sample; and an output device to output the plurality of wavelengths detected by the spectrometer.

4. The system of claim 3, wherein the detector further comprises additives usable to lower an electrical resistance of the sample, and wherein the energy source is a voltage or light source.

5. The system of claim 4, wherein the plurality of wavelengths output by the detector is usable to determine a flow rate of the produced wellbore fluid.

6. The system of claim 5, wherein at least one of the first tracer or the second tracer is in a propping agent positionable in a hydraulic fracturing fluid usable in a hydraulic fracturing process in the wellbore, and wherein the detector is positionable proximate to the surface of the wellbore to analyze a sample of the hydraulic fracturing fluid.

7. The wellbore tracer system of claim 1, wherein the first layer and the second layer of the first tracer are bound within a binder that comprises a dissolvable material configurable to dissolve into the produced wellbore fluid to release the first type of metal ions or the second type of metal ions.

8. The wellbore tracer system of claim 7, wherein the binder comprises at least one of a thermoplastic, a thermoset, or an elastomer.

* * * * *